United States Patent [19]
Detty

[11] Patent Number: 4,474,573
[45] Date of Patent: Oct. 2, 1984

[54] KNEE SLEEVE

[76] Inventor: Garnett E. Detty, 525 General Muhlenberg Rd., King of Prussia, Pa. 19406

[21] Appl. No.: 351,717

[22] Filed: Feb. 24, 1982

[51] Int. Cl.³ .............................................. A61F 3/00
[52] U.S. Cl. ........................................ 128/80 C; 2/24
[58] Field of Search ................ 128/80 C, 80 R, 87 R; 2/22, 24

[56] References Cited

U.S. PATENT DOCUMENTS

| | | | |
|---|---|---|---|
| 1,587,508 | 6/1926 | Coats | 2/24 |
| 4,084,584 | 4/1978 | Detty | 128/80 C |
| 4,250,578 | 2/1981 | Barlow | 2/24 |

*Primary Examiner*—Stephen C. Pellegrino
*Attorney, Agent, or Firm*—Caesar, Rivise, Bernstein & Cohen

[57] ABSTRACT

A sleeve adapted to be placed over the knee, said sleeve being configured to anatomically conform to the thigh, knee and upper calf. The sleeve comprises a resilient elastomeric foam sheath having a fabric covering, with the elastomeric foam being adapted to contact the leg. The sheath is formed from a front panel and a rear panel, with the rear panel being basically diamond-shaped, and having upper and lower apices adapted to be positioned in the center of the rear of the leg. The front panel has side edges angled inwardly from the top and bottom, and the rear panel is secured to the front panel along the side edges of the front panel. The sleeve can include an opening over the patella, which permits the patella to project into the opening.

12 Claims, 7 Drawing Figures

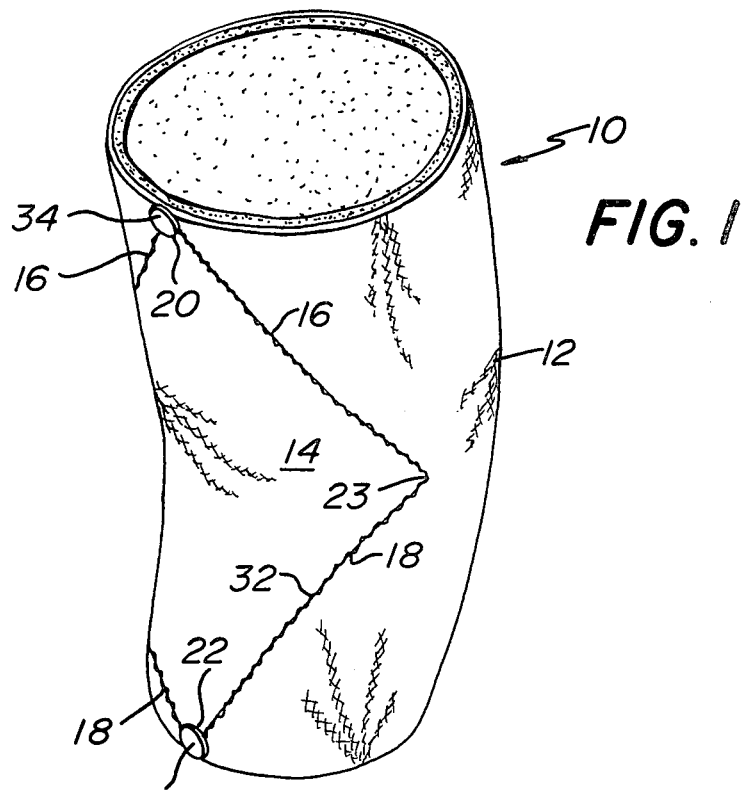
FIG. 1
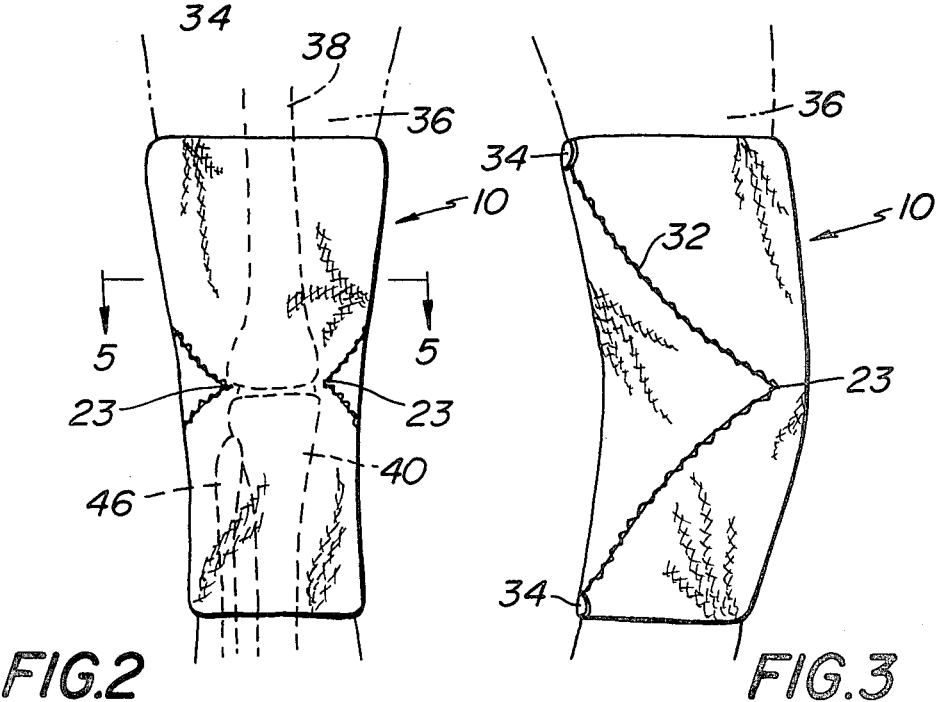
FIG.2
FIG.3

KNEE SLEEVE

This invention relates to a knee sleeve, and more particularly, to a sleeve that is particularly adapted to restrain the knee during normal and athletic activities, while at the same time, providing total comfort to the user of the sleeve when the knee is bent.

Various devices have been developed to restrict the knee, especially during normal knee movements in the practice of athletics. Most commonly, these devices are used on injured, unhealthy or congenital knee problems which exhibit atrophy or weakness. These problems can result from an athletic or other injury, or through such problems as arthritis. The various devices now in use were developed to protect the damaged knee, or to give comfort to the person who has a damaged or afflicted knee.

Applicant has developed a number of knee sleeves that have proven to be most effective for use on an afflicted knee. One of the problems that applicant has recognized in connection with his own knee sleeves and those of his competitors is irritation from seams at the back of the knee, which is called the popliteal area. To some people, this irritation can be sufficient enough to even cause open sores. A common design for a knee sleeve that can cause such problems is a sleeve formed from a single panel of elastomeric foam wherein there is a back vertical seam in the center and a horizontal seam in the center which intersects with the back vertical seam. This configuration can cause considerable problems when the knee is placed in extreme flexion, when it is bent. At times of extreme flexion, the neoprene bunches in the popliteal area, and the combination of the bunching and the pressing of the seams against the popliteal area can cause irritation. These problems will most commonly occur when there is constant bending of the knee, such as during bicycling. running or wrestling. The problem is also encountered by football linemen when they are in their crouching stance. Although the problem is not as severe for basketball players, it is still encountered when the player is sitting on the bench.

The bunching and irritation problem was greatly minimized by replacing the vertical and intersecting horizontal seams in a single panel by two panels which are joined together by spaced vertical seams in the back of the sleeve. This configuration for a knee sleeve is shown in applicant's prior U.S. Pat. No. 4,084,584. Even though the device shown in U.S. Pat. No. 4,084,584 provided a marked improvement over the single vertical seam sleeve, the improved sleeve still had a number of shortcomings. One of the shortcomings is the fact that the sleeve could be formed with only a slight bent-knee configuration, and this affected the flexion of the knee. The other problem is that weak points arose at the tops and bottoms of the stitching securing the two panels together. This provided a stress point, which could tear under hard use.

The knee sleeve of this invention eliminates all of the aforementioned problems of the prior knee sleeves.

In an effort to obviate the problem of popliteal irritation cause by bunching or seams in a knee sleeve, applicant developed and sold a knee sleeve comprising a front panel and two angled back panels that crossed in the popliteal area. The two back panels are stitched to the front panel, and one projects downwardly in the back and the other projects upwardly in the back, with one panel overlying the other. The edges of the back panels are secured to the edges of the front panel. This design is effective in eliminating popliteal irritation, but has other shortcomings. The major shortcoming of this design is the fact that there is insufficient space to provide a patella opening in the front panel. This is because this design requires two vertically extending reinforcing rods in the front panel in order to permit the front panel to retain its shape. Because of the presence of the reinforcing rods, there is insufficient space to place a patella opening in the front panel.

The knee sleeve of the instant invention can be made with or without a patella opening. As explained in aforementioned U.S. Pat. No. 4,084,584, the patella opening in a knee sleeve is used to treat chondromalacia of the patellofemoral joint. This condition is defined as an irregular undersurface of the patella, which condition is painful and disabling when the knee is flexed and extended. The opening removes all pressure from the patella, and the patella is free to rise within the opening. With the pressure removed, the remaining pressures around the knee, particularly from the popliteal area, force fluid to the underside, or irritated side, of the freed patella. This apparently elevates the patella and provides a lubricant for patella movement when the knee is flexed and extended.

Accordingly, the knee sleeve of this invention eliminates substantially all of the irritation in the poplitel area caused by seams or bunching of the elastomeric foam when the knee is flexed. The angling of the stitching of the edges of the rear panel relative to the edges of the front panel greatly reduces any possibility of tearing of the seams during hard use of the knee sleeve. Thus, the bending of the knee is at an angle to the seams, rather than in alignment with the seams, which could cause tearing of the seams.

It is accordingly an object of this invention to provide a novel knee sleeve.

It is another object of this invention to provide a knee sleeve adapted to avoid irritation of the popliteal area during wearing and during bending or flexing of the knee.

It is a further object of this invention to provide a knee sleeve formed from two panels, with the panels configured to avoid undue stress on the seams joining the two panels.

These and other objects of this invention are accomplished by providing a sleeve adapted to be placed over the knee, said sleeve being configured to anatomically conform to the thigh, knee and upper calf, said sleeve comprising a resilient elastomeric foam sheath having a fabric covering, said sheath being formed from a front panel and a rear panel, said rear panel having an upper terminus and a lower terminus and inclined edges projecting outwardly from said termini, said front panel having edges angled to complement the edges of said rear panel, and said front and rear panels being secured together along said edges.

Other objects and many of the attendant advantages of this invention will be readily appreciated as the same becomes better understood by reference to the following detailed description when considered in connection with the accompanying drawing wherein:

FIG. 1 is a perspective view of the knee sleeve of this invention, looking from the rear thereof;

FIG. 2 is a front elevational view of the knee sleeve of this invention, shown on the right leg of the wearer;

FIG. 3 is a side elevational view of the knee sleeve shown in FIG. 2;

Figure 4:
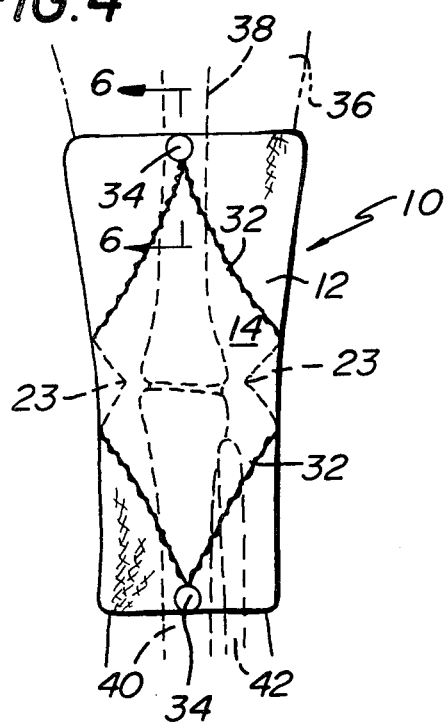
FIG. 4 is a rear elevational view of the knee sleeve shown in FIG. 2.

Referring now in greater detail to the various figures of the drawing wherein like reference characters refer to like parts, a knee sleeve embodying the present invention is generally shown at 10 in FIG. 1. Sleeve 10 basically comprises a front panel 12 and a rear panel 14 secured thereto.

Panel 12 includes upper inclined edges 16 and lower inclined edges 18. The upper portion of panel 12 is wider than the lower portion of panel 12 in order to conform snugly to the thigh and the calf. Thus, as is obvious, the thigh has a larger circumference than the calf.

Back or rear panel 14 has a diamond shape, and includes upper apex or terminus 20, lower apex or terminus 22 and side termini 23.

Panels 12 and 14 are formed from the same material, which material comprises a resilient elastomeric foam 24 (FIG. 5) and a covering of a knit fabric 26. The resilient elastomeric foam 24 can comprise any of the foams known to the art, such as rubber, neoprene, latex and polyurethane foams. The fabric is knit, so that it will have inherent elastic properties. Preferably, the fabric is formed form synthetic yarns, such as nylon, to aid in durability and abrasion resistance. However, natural fibers, such as cotton, can also be used. Any of the knit fabrics known to the art can be used, such as circular knit fabrics or tricots. The fabric is bonded to the foam by any of the known processes, such as flame lamination or adhesive bonding. The foam is also stretchable, and is capable of stretching in all directions, as is the fabric.

Figure 5:
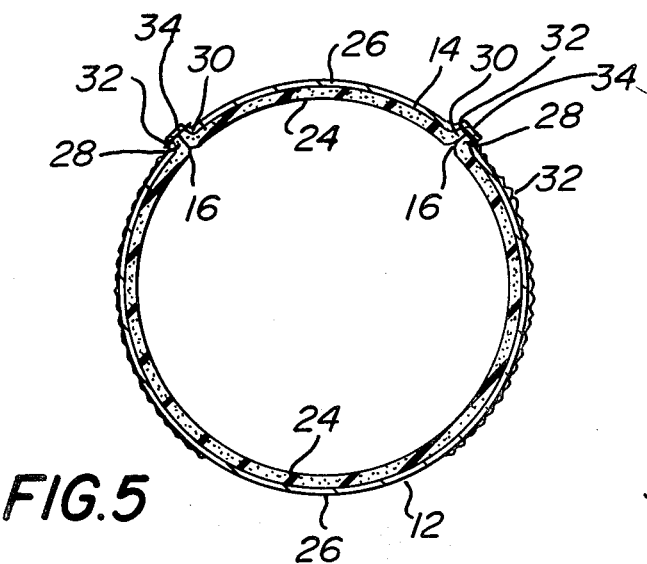
FIG. 5 is an enlarged sectional view taken along the line 5—5 of FIG. 2.
Figure 6:
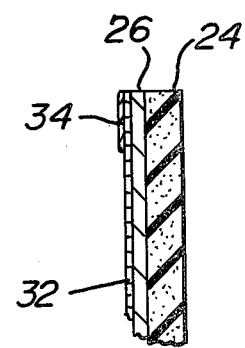
FIG. 6 is an enlarged sectional view taken along the line 6—6 of FIG. 4.

The knee sleeve 10 is assembled by securing the rear panel 14 to the front panel 12. As seen in FIG. 5, during the securement, the upper edges 16 of front panel 12 are bent outwardly to form lips 28. Similarly, the upper edges of rear panel 14 are bent outwardly to form lips 30. The bending of the lips is easily accomplished in view of the highly flexible nature of the foam 24 and its fabric facing 26. Prior to forming the lips 28 and 30, a coating of adhesive is applied to those portions of the front and rear panels forming the lips. Any conventional rubber or neoprene adhesive can be used for this purpose. These adhesives are well-known to the art. Although not shown in FIG. 5, similar lips are formed in lower edges 18 of front panel 12 and the lower edges of rear panel 14, and these lips are also adhesively secured together.

After applying the adhesive, the rear panel 14 is secured to the front panel 12 by stitching 32. The stitching is carried out with a heavy, durable yarn, such as nylon. The type of stitch can be any stretchable stitch. This enables the stitching to stretch along with the foam and fabric laminate when the knee sleeve is in flexion. In the embodiment of the invention shown, the stitch is a Bonus stitch, although other types of stretchable stitching can be used. Four lines of stitching are used, with the stitching commencing at each terminus or apex 20 and 22, and ending at each side terminus 23.

It has been found in the prior knee sleeves that a problem can arise with the unraveling of stitching securing the panels of the knee sleeves together at the points where the stitching commences. This problem occurs at the tops and bottoms of the lines of stitching in the rear of the knee sleeves. The problem is most acute when the knee sleeves are subjected to hard use, and during continual bending of the leg. The problem is obviated by the stitching design used in the knee sleeve of this invention. Thus, rather than having the stitching project along or parallel to the vertical axis of the knee sleeve, which is done with the prior knee sleeves, the stitching projects at an angle to the vertical axis, as is apparent from FIGS. 1 and 4. Thus, there is less tendency to rupture the stitching, since the stitching will expand partially in the direction of bending, rather than being aligned with the direction of bending.

Furthermore, since the weak points in the stitching occur at the points where the stitching commences along the vertical axis of the knee sleeve, to further reinforce the stitching, patches 34 are provided. Patches 34 are formed from discs of fabric which are identical in composition and color to the fabric facing 26 on the foam 24. The fabric discs are provided with a hot melt adhesive on the rear face thereof, and are secured in place at the commencement points of the stitching using a hot iron. This causes the adhesive to fuse to the stitching and the associated fabric facing 26, and provides a protection for the commencement points of the stitching to further prevent any rupturing or unraveling of the stitching.

The knee sleeve 10 is shown in FIGS. 2 to 4 as being positioned on the right leg 36. The bones of the right leg are shown in phantom, and include the femur or thighbone 38, the tibia or shinbone 40 and the fibula 42. The bones also include the knee cap or patella, which has not been shown, for the sake of clarity.

As further seen in FIGS. 2 to 4, the shape of the knee sleeve permits the sleeve to anatomically conform to the thigh, knee and upper calf. Thus, the upper portion of the knee sleeve is flared outwardly to conform to the thigh, which has a larger circumference than the calf.

During the use of knee sleeve of this invention, the resilient foam 24 is in contact with the skin of the wearer. It has been found that where there is a fabric lining on the interior of the knee sleeve, the knee sleeve will tend to slip during active use of the leg. In the sleeve of this invention, there is sufficient friction between the foam and the skin of the leg to prevent any slippage during use.

One of the advantages of the prior art knee sleeves which included a fabric lining was that the knee sleeve could more easily be pulled in place. However, it has been found that merely having the fabric facing 26 on the outside is sufficient to allow for the easy application of the knee sleeve. The knee sleeve of this invention is best applied by turning it inside out, that is, having the fabric on the inside. The knee sleeve is then slid on the leg by having the lower end upper most, and the sliding is continued until the lower end is at a position where it will ultimately rest when the knee sleeve is fully in place. The upper end of the sleeve, which at this point is lowermost, is then pulled upwardly, which results in turning the foam side inwardly. This in turn results in turning the knee sleeve to a condition where the correct or fabric side is outward, and places the larger end on the thigh, in the position shown in FIGS. 2 to 4. To aid in applying the knee sleeve, lubricating powders, such as talcum, corn starch or baking soda, should be liberally applied to the leg on which the knee sleeve will be used.

In addition to aiding in the placing of the knee sleeve on the leg, the fabric laminated to the foam also gives the foam dimensional stability and preserves the foam from deteriorating due to abrasion.

In view of the inherent elasticity of the foam and fabric laminate, the knee sleeve can fit a range of knee sizes. However, different sized knee sleeves can be formed to accomodate large differences in leg dimensions, with each size being able to accomodate a range of knee circumferences of 1 to 2 inches (2.54 to 5.08 cm).

The foam and fabric laminate of the knee sleeve of this invention can be used in any standard thicknesses, such as ⅛ inch (0.318 cm), 3/16 inch (0.476 cm) or ¼ inch (0.635 cm). The preferred thickness is ⅛ inch (0.318 cm).

As is apparent in FIGS. 1 and 3, during the bending of the leg, a substantially smooth rear surface of the knee sleeve will be provided by the rear panel 14. The stitching 32 is basically along the lines of bending, and no irritation is provided by the seams where the stitching is made. Another feature of the stitching is that the termini 23 extend around to the front of the leg, as apparent in FIG. 2. In wearing the knee sleeve, all of the compression of the foam and fabric laminate will occur in the rear of the knee sleeve or on the sides of the leg and sleeve. By having the termination of the stitching at a point forward of the bending motion prevents any interference with the bending caused by the stitching. If the stitching were placed farther to the rear of the leg, when the leg is bent, it has been found that the foam would tend to bunch in the area immediately in front of the stitching. This will not occur in the knee sleeve of this invention, since the stitching terminates at a point forwardly of the bend line.

Another comfort feature of the knee sleeve of this invention is the fact that the sleeve is formed with a slightly bent configuration, as seen in FIGS. 1 and 2. The amount of bend can be varied by varying the angles at which the edges of the front and rear panels are cut. Having the bent configuration facilitates the bending of the knee during use of the sleeve.

It is thus seen that the knee sleeve of this invention provides a smooth surface which permits total freedom in bending while wearing the same, while at the same time, avoiding any irritation in the bend area caused by bunching of the foam or by seam irritation. The angling of the seams transversely to the angle of bending reduces the possibility of seam rupture during bending.

Figure 7:
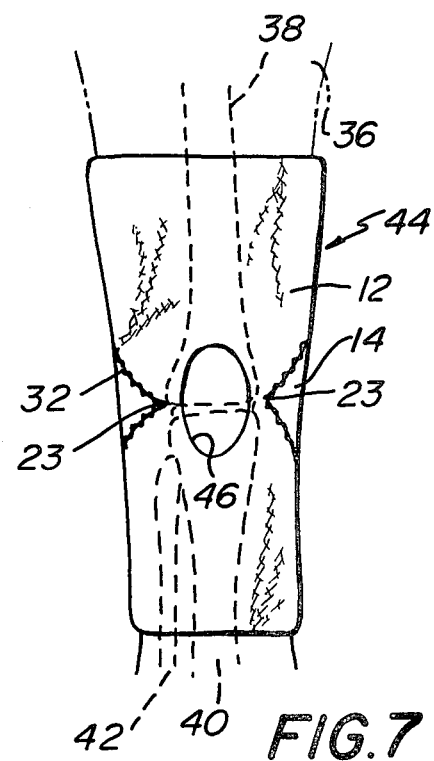
FIG. 7 is a front elevational view of the knee sleeve of this invention, and containing a patella opening.

In FIG. 7, a modified embodiment of the knee sleeve of this invention is generally shown at 44, as positioned on a right leg 36. Knee sleeve 44 is identical in all respects to knee sleeve 10, with the exception of the fact that an opening 46 is formed in front panel 12. The purpose of the opening 46 is to permit the patella of the leg to project therethrough. Patella openings are known in prior art knee sleeves, and an embodiment of a knee sleeve showing a patella opening in a knee sleeve can be found in applicant's prior U.S. Pat. No. 4,084,584. The knee sleeve of this invention is adapted to be provided with a patella opening where one is necessary. As pointed out above, in one of applicant's prior knee sleeves which was designed to reduce popliteal irritation, it was not possible to provide a patella opening. This is the knee sleeve that includes the crossed rear panels with the front reinforcing bars.

The purpose of the patella opening 46 is to reduce the friction of the patella during flexion and extension of the knee when the patella is suffering from chondromalacia. Thus, the patella can move forwardly in the knee sleeve, since the pressure over the patella is removed. This permits fluid to flow behind the patella and lubricate the patella when the user of the knee sleeve is actively engaged in any activity requiring leg movement, such as cycling, jogging, tennis, football, etc.

Accordingly, when chondromalacia does not present a problem, the embodiment of this invention generally shown at 10 can be utilized. Where chondormalicia does present a problem, the embodiment of the invention generally shown at 44 can be utilized.

Without further elaboration, the foregoing will so fully illustrate my invention that others may, by applying current or future knowledge, readily adapt the same for use under various conditions of service.

I claim:

1. A sleeve adapted to be placed over the knee, said sleeve being configured to anatomically conform to the thigh, knee and upper calf, said sleeve comprising a resilient elastomeric foam sheath having a fabric covering, said sheath being formed from a front panel and a rear panel, said rear panel having an upper terminus and a lower terminus and inclined edges projecting outwardly from said termini, said front panel having edges angled to complement the edges of said rear panel, said rear panel being in the shape of a diamond, with the upper and lower apices of said diamond being positioned approximately in the center of the rear longitudinal axis of said sleeve, said rear panel further including side termini, said side termini extending forwardly into said front panel to a position wherein they will be positioned on the front portion of the knee when said sleeve is placed on the leg of the user of the sleeve, and said front and rear panels being secured together along said edges.

2. The sleeve of claim 1, wherein said panels are secured together by stitching.

3. The sleeve of claim 2, wherein said stitching has commencement points at each of said upper and lower termini, and further including means to aid in preventing said stitching from unraveling or rupturing at said upper and lower termini.

4. The sleeve of claim 1, and further including an opening in said front panel, said opening being adapted to permit the patella to project therethrough when the sleeve is on a user's leg.

5. The sleeve of claim 1, wherein said elastomeric foam is on the interior of said sleeve, and is adapted to contact the leg during use.

6. The sleeve of claim 5, wherein said elastomeric foam is neoprene foam.

7. The sleeve of claim 1, wherein said fabric is a knit fabric.

8. The sleeve of claim 7, wherein said knit fabric comprises nylon.

9. A sleeve adapted to be placed over the knee, said sleeve being configured to anatomically conform to the thigh, knee and upper calf, said sleeve comprising a resilient elastomeric foam sheath having a fabric covering, said sheath being formed from a front panel and a rear panel, said rear panel having an upper terminus and a lower terminus and inclined edges projecting outwardly from said termini, said front panel having edges angled to complement the edges of said rear panel, said front and rear panels being secured together along said edges by stitching, said stitching having commencement points at each of said upper and lower termini, and further including means to aid in preventing said stitching from unraveling or rupturing at said upper and lower termini, said means comprising a fabric disc overlying each of said commencement points, with said fabric discs being secured to said stitching at said commencement points and to the outer surface of said sleeve.

10. The sleeve of claim 9, wherein said fabric discs are adhesively secured in place.

11. A sleeve adapted to be placed over the knee, said sleeve being configured to anatomically conform to the thigh, knee and upper calf, said sleeve comprising a resilient elastomeric foam sheath having a fabric covering, said sheath being formed from a front panel and a rear panel, said rear panel having an upper terminus and a lower terminus and inclined edges projecting outwardly from said termini, said front panel having edges angled to complement the edges of said rear panel, said rear panel being in the shape of a diamond, with the upper and lower apices of said diamond being positioned approximately in the center of the rear longitudinal axis of said sleeve, said front and rear panels being secured together along said edges by stitching, wherein said stitching commences at each of said upper and lower apices, and further including fabric discs overlying and secured at said commencement points of said stitching to aid in preventing the unraveling or rupturing of said stitching.

12. The sleeve of claim 11, wherein said fabric discs are adhesively secured in place.

* * * * *